United States Patent [19]

Berges

[11] 3,943,129

[45] Mar. 9, 1976

[54] 7-AMINO-3-(1,3,4-THIADIAZOLINYLTHIO-METHYL) CEPHALOSPORINS

[75] Inventor: David Alan Berges, Audubon, Pa.

[73] Assignee: SmithKline Corporation, Philadelphia, Pa.

[22] Filed: Dec. 3, 1974

[21] Appl. No.: 529,142

Related U.S. Application Data

[62] Division of Ser. No. 306,507, Jan. 14, 1972, Pat. No. 3,868,369.

[52] U.S. Cl. .............................. 260/243 C; 424/246
[51] Int. Cl.$^2$ ........................................ C07D 501/36
[58] Field of Search ................................ 260/243 C

[56] References Cited
UNITED STATES PATENTS 3,850,916    11/1974    Crast............................... 260/243 C Primary Examiner—Richard J. Gallagher
Assistant Examiner—David E. Wheeler
Attorney, Agent, or Firm—Stuart R. Suter; Alan D. Lourie; William H. Edgerton

[57] ABSTRACT

Cephalosporins containing a heterocyclicthiomethyl group at position 3 are prepared. The heterocyclic group is 5-oxo-$\Delta^2$-1,2,4-triazolinyl, 5-thiono-$\Delta^2$-1,2,4-triazolinyl, 5-oxo-$\Delta^2$-1,2,4-thiadiazolinyl or 5-thiono-$\Delta^2$-1,3,4-thiadiazolinyl. The compounds have antibacterial activity.

3 Claims, No Drawings

7-AMINO-3-(1,3,4-THIADIAZOLINYLTHIO-METHYL) CEPHALOSPORINS

This is a division of application Ser. No. 306,507 filed Nov. 14, 1972, now U.S. Pat. No. 3,868,369.

This invention relates to novel cephalosporin compounds that have improved properties. These compounds have antibacterial activity.

The compounds within the scope of the invention are represented by the structural formula

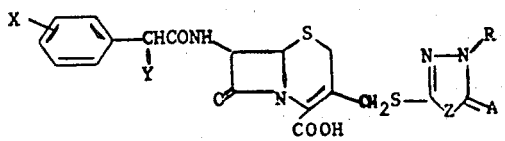

where X is H, $CH_2OH$, SH, or OR;
Y is $NH_2$ or OH;
Z is NR or S;
A is O or S; and
R is hydrogen or $C_1$-$C_4$ alkyl.

Preferred compounds are those having a phenylglycine or mandelic acid substituent at position 7, both of which may be unsubstituted or substituted with a p-hydroxy group. Preferred heterocyclic systems at position 3 are those where Z is nitrogen and A is oxygen, Z is nitrogen and A is sulfur, and Z and A are both sulfur.

Cephalosporins with many and varied substituents are known in the prior art. As related to this invention, cephalosporins that come within the following general formula are described in several patents

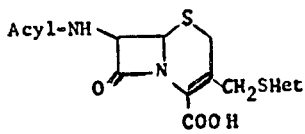

In particular, U.S. Pat. 3,641,021 discloses compounds where Acyl is α-aminophenylacetyl or mandeloyl and Het is thiadiazolyl and tetrazolyl. In Belgian Pat. 776,622, Acyl is α-aminophenylacetyl and mandeloyl and Het is 1,2,4-triazolyl or other heterocyclic systems. U.S. Pat. 3,687,948 and Belgian Patent 778,207 claim compounds where Acyl is α-aminophenylacetyl and Het is oxazolyl or 1,2,3-triazolyl, respectively. Compounds where Acyl can be any of various heterocyclicacetyl systems and Het is 1,2,4-triazolyl, 1,3,4-thiadiazolyl or numerous other heterocyclic systems are disclosed in U.S. Pat. Nos. 3,516,997 and 3,530,123. In all the above prior art, however, the oxo or thiono substituent is not present on any of the heterocyclic systems. U.S. Pat. 3,278,531 broadly discloses cephalosporins with many types of substituents at 7 and numerous sulfur-containing groups, both cyclic and acyclic, at 3. Within this patent is a mercaptohydantoin, a group that distinctly differs from the oxoheterocyclic systems of this invention and for which no distinct properties were claimed. Cyclic thioureas were stated not to be within the scope of the patent.

It has now been found that the compounds with these oxo or thiono substituents have greater stability than the prior art compounds that do not have these substituents. For example, 7-(α-aminophenylacetamido)-3-(5-oxo-Δ²-1,2,4-triazolin-3-ylthiomethyl)-3-cephem-4-carboxylic acid is more stable in solution at neutral or basic pH than any prior art compounds that were tested. Also, the compound has greater stability to copper ion than tested prior art compounds.

Compounds of this invention are prepared from 7-aminocephalosporanic acid (7-ACA) by standard methods well known in the art. The acetoxy group of 7-ACA is displaced with the appropriate heterocyclicthione compound and the 7-amino group is acylated with the phenylglycine or mandelic acid or an activated derivative thereof. The order of these two reactions is not critical although the usual sequence is displacement followed by acylation. With some compounds the reverse order may be preferred; however, this choice is well within the ability of one skilled in the art.

The displacement reaction is run in a water: acetone or similar solvent system at the reflux temperature of the solvent. The solution is maintained at a pH near neutrality. The product is isolated by standard methods.

Prior to the acylation, the α-hydroxy and amino groups of the mandelic acid or phenylglycine must be protected with an easily removable protecting group. Many protecting groups are known and used in the art, for example, dichloroacetyl, tetrahydropyranyl, or trimethylsilyl are used for hydroxy groups and t-butoxycarbonyl, benzyloxycarbonyl, trichloroethoxycarbonyl, or similar group commonly used in peptide synthesis are used for amino groups. In addition, prior to acylation, the carboxyl group is activated by its conversion to an activated derivative such as the acid chloride, mixed anhydride, or an activating ester. If the carboxyl group of the 7-aminocephalosporin is protected, the acylation may be effected using a coupling reagent such as dicyclohexylcarbodiimide. Following acylation, any protecting groups are removed in the usual manner.

Starting materials for the product compounds of this invention are commercially available, prepared by known methods, or described herein. The heterocyclic compounds used in the displacement reaction are prepared by published methods or by variations of known methods that would be apparent to one skilled in the art. The preparation of 1,2,4-triazolidin-5-one-3-thione and its 4-alkyl derivatives is described in Chem. Ber., 56, 1370 (1923) and J. Org. Chem., 23, 618 (1958). The 1-alkyl derivatives are prepared by sodium borohydride reduction of the appropriate thiosemicarbazone to give the 1-alkylthiosemicarbazide which is reacted with ethyl chloroformate and then a strong base. The synthesis of 1,2,4-triazolidin-3,5-dithione is reported in Ann., 426, 313 (1921). The 1,3,4-thiadiazolidin-5-one-2-thione is prepared analogously to known methods [Chem. Ber., 27, 2507 (1894)] while the dithione analog is commercially available.

Optical isomerism will exist in the side chain at position 7 due to the presence of the assymetrical carbon atom. While the D isomer is preferred, the L isomer and the racemic mixture are within the scope of this invention. In addition, it is recognized that the oxo and thiono substituents on the heterocyclic group may exist in other tautomeric forms, i.e. the hydroxy or mercapto. The compounds may exist exclusively as one tautomer or may be in equilibrium between the other forms; however, these are all included within the scope of this invention.

The compounds are antibacterial agents with activity against both Gram-positive and Gram-negative bacteria. Minimum inhibitory concentrations (MIC) ranged from 0.1 to greater than 200 µg/ml. Table I shows the MIC's against a representative group of bacteria for 7-(α-aminophenylacetamido)-3-(5-oxo-$\Delta^2$-1,2,4-triazolin-3-ylthiomethyl)-3-cephem-4-carboxylic acid (I), 7-(α-aminophenylacetamido)-3-(4-methyl-5-oxo-$\Delta^2$-1,2,4-triazolin-3-ylthiomethyl)-3-cephem-4-carboxylic acid (II), 7-(α-aminophenylacetamido)-3-(4-ethyl-5-oxo-$\Delta^2$-1,2,4-triazolin-3-ylthiomethyl)-3-cephem-4-carboxylic acid (III), 7-(α-amino-p-hydroxyphenylacetamido)-3-(5-oxo-$\Delta^2$-1,2,4-triazolin-3-ylthiomethyl)-3-cephem-4-carboxylic acid (IV), 7-mandelamido-3-(5-oxo-$\Delta^2$-1,2,4-triazolin-3-ylthiomethyl)-3-cephem-4-carboxylic acid (V), 7-mandelamido-3-(4-methyl-5-oxo-$\Delta^2$-1,2,4-triazolin-3-ylthiomethyl)-3-cephem-4-carboxylic acid (VI), and 7-mandelamido-3-(5-thiono-$\Delta^2$-1,3,4-thiadiazolin-2-ylthiomethyl)-3-cephem-4-carboxylic acid (VII). Data for known cephalosporins, cephaloridine (S-I) and cephalexin (S-II), are included as representative standards. In vivo studies in Table 2, giving $ED_{50}$ values for the same compounds when administered to infected mice subcutaneously, also show the high activity of these compounds. Compounds with the α-amino-p-hydroxyphenylacetamido group at position 7 have the special advantage of oral activity. Compound IV showed a $ED_{50}$ of 9.5 and 6.2 mg/kg against E. coli and Kleb. pneumonia, respectively, in infected mice when the compound was administered orally.

known and are obvious to one skilled in the art. The nontoxic pharmaceutically acceptable salts of the compounds are useful for the same purposes as the free components and are therefore within the scope of the invention.

The following examples are presented to illustrate the invention and are not to be considered limitative.

EXAMPLE 1

7-(α-Aminophenylacetamido)-3-(5-oxo-$\Delta^2$-1,2,4-triazolin-3-ylthiomethyl)-3-cephem-4-carboxylic acid In a mixture of water (40 ml) and acetone (10 ml) was dissolved in 7-ACA (2.73 g, 0.01 mol) and NaHCO$_3$ (1.61 g, 0.02 mol) and then 1,2,4-triazolidin-5-one-3-thione (1.76 g, 0.015 mol) in acetone (20 ml) was added. Solid NaHCO$_3$ was added to adjust the mixture to pH 7 and give complete solution. The reaction was refluxed for 2 hours and then allowed to cool to room temperature. The solution was cooled with ice, adjusted to pH 3.5 with 3N HCl, and filtered. The collected solid was washed with water and acetone, and then the solid was dissolved in 3N HCl (15 ml). After filtering, the filtrate was treated with decolorizing carbon, filtered, and adjusted to pH 3.5. The solid was collected, washed with water and acetone, and dried to give the 7-amino-3-(5-oxo-$\Delta^2$-1,2,3-triazolin-3-ylthiomethyl)-3-cephem-4-carboxylic acid.

To a solution of dry THF (92 ml) containing triethylamine (3.2 ml, 0.023 ml) was added N-t-butoxycar-

TABLE I

| Bacteria | MIC (µg/ml) | | | | | | | | |
|---|---|---|---|---|---|---|---|---|---|
| | I | II | III | IV | V | VI | VII | S-I | S-II |
| S. aureus HH 127 | 1.6 | 6.3 | 3.1 | 6.3 | 0.8 | 1.6 | 0.8 | 0.4 | 3.1 |
| S. aureus SK 23390 | 1.6 | 3.1 | 3.1 | 6.3 | 0.4 | 0.4 | 0.4 | 0.1 | 1.6 |
| Strep. pyog. C203 | 0.1 | 0.1 | 0.1 | 0.1 | 0.1 | 0.1 | 0.2 | 0.1 | 0.1 |
| Strep. faecalis HH 34358 | 50 | 50 | 25 | 100 | 50 | 25 | 25 | 6.3 | 50 |
| E. coli SK 12140 | 3.1 | 12.5 | 12.5 | 6.3 | 3.1 | 6.3 | 1.6 | 3.1 | 6.3 |
| E. coli HH 33779 | 6.3 | 25 | 12.5 | 25 | 6.3 | 12.5 | 3.1 | 6.3 | 6.3 |
| Kleb. pneumo. SK 4200 | 3.1 | 6.3 | 6.3 | 6.3 | 3.1 | 3.1 | 1.6 | 3.1 | 6.3 |
| Kleb. pneumo. SK 1200 | 3.1 | 6.3 | 6.3 | 12.5 | 1.6 | 3.1 | 0.8 | 3.1 | 3.1 |
| Pseudomonas sp. HH 63 | >200 | >200 | >200 | >200 | >200 | >200 | >200 | >200 | >200 |
| Sal. paratyphi ATCC 12176 | 1.6 | 3.1 | 3.1 | 6.3 | 1.6 | 3.1 | 0.8 | 1.6 | 3.1 |
| Shig. paradys. HH 127 | 3.1 | 6.3 | 6.3 | 12.5 | 1.6 | 0.1 | 1.6 | 1.6 | 6.3 |
| Entero. aerogenes ATCC13048 | 6.3 | 25 | 25 | 12.5 | 12.5 | 12.5 | 12.5 | >200 | 12.5 |
| Entero. cloaca Pa.S.L.969 | 12.5 | 50 | 25 | — | 12.5 | — | — | >200 | 6.3 |
| Serrantia marcescens ATCC 13880 | 200 | >200 | 200 | >200 | >200 | >200 | 200 | >200 | 50 |
| Staph. aurcus villaluz | 12.5 | 25 | 25 | 25 | 25 | 12.5 | 12.5 | 12.5 | 50 |

TABLE 2

| Compound | $ED_{50}$ (mg/kg) | |
|---|---|---|
| | E. coli SK 12140 | Kleb. pneumo. SK 4200 |
| I | 2.9 | 7 |
| II | 12.5 | 11.5 |
| III | 29 | 92 |
| IV | 4 | 2.8 |
| V | 4 | 8.7 |
| VI | 9 | 21 |
| VII | 21.5 | 64 |
| S-I | 6 | 7.6 |
| S-II | 12 | 25 |

The compounds are administered for the treatment and prevention of bacterial infections by injection or oral methods. Methods of formulation and administration are the same as for other known cephalosporin compounds and are within the skill of the art.

Due to the presence of the acid and amino functions in these compounds, salts can be prepared by known methods. Methods to prepare the acid or base salts or to convert the salts to the free compound are well bonylphenylglycine (5.8 g, 0.023 mol). After cooling to −10°, isobutylchloroformate (3.0 ml, 0.023 mol) was added and the reaction solution was stirred for 30 minutes. A solution of above 7-aminonucleus (7.57 g, 0.023 mol) and triethylamine (4.2 ml) in 50% aqueous THF (84 ml) was added over a 25 minute period −10°. The reaction was stirred 20 minutes at −5°, 40 minutes at 5°, and 30 minutes at room temperature and then the THF was removed in vacuo. The aqueous residue was diluted with water (140 ml) and extracted with ethyl acetate. The water phase was adjusted to pH 3.5 while being cooled, ethyl acetate was added and the mixture was acidified to pH 2.5. A gummy solid was collected and discarded. The aqueous phase of the filtrate was separated and extracted with ethyl acetate again. The combined extracts were washed with water, dried, and evaporated to a foam to which ether was added and a solid was collected. Acetone was added to the product and a solid precipitated from the solution after standing 45 minutes. The pure N-protected product was collected and dried.

The above product (5.0 g) was stirred with cold trifluoroacetic acid (50 ml) for 45 minutes, the ice bath was removed, and the stirring was continued for 45 minutes. The trifluoroacetic acid was evaporated in vacuo, and the residue was triturated with ether to give a solid which was dissolved in water (50 ml). The aqueous solution was covered with methyl isobutyl ketone and adjusted to pH 1.9 with tributylamine. The pure title compound precipitated.

EXAMPLE 2

7-Mandelamido-3-(5-oxo-$\Delta^2$-1,2,4-triazolin-3-ylthiomethyl)-3-cephem-4-carboxylic acid A solution of the 7-amino nucleus from Example 1 (7.0 g, 0.0213 mol) in a mixture 3% NaHCO$_3$ (160 ml) and water (160 ml) was cooled to −15° and then O-dichloroacetylmandeloyl chloride (12.0 g, 0.0426 mol) was added over a 40 minute period during which time the pH was maintained at 5.5 using 10% NaOH. The reaction was allowed to warm to 0° over a 30 minute period and was stirred at 0° for one hour. The solution was filtered, extracted with ether, covered with ethyl acetate, adjusted to pH 3, and extracted with ethyl acetate. The extracts were dried and evaporated to an oil which solidified when triturated with ether. The solid was dissolved in ethyl acetate and concentrated to a volume of 30 ml which was added dropwise with stirring to ether (300 ml) to give a solid which was collected and dried. A solution of the solid in methanol was adjusted to pH 9.6 with a 5% solution of sodium methoxide in methanol and stirred for 30 minutes. 2-Ethylhexanoic acid was added until pH 7 was reached. The reaction was filtered, diluted with ethyl acetate (150 ml) and filtered again. The filtrate was concentrated and diluted with more ethyl acetate to give the solid title compound.

EXAMPLE 3

7-($\alpha$-Aminophenylacetamido)-3-(4-methyl-5-oxo-$\Delta^2$-1,2,4-triazolin-3-ylthiomethyl)-3-cephem-4-carboxylic acid 7-ACA (27.23 g, 0.1 mol) was suspended in water (200 ml) and acetone (100 ml) and then a solution of NaHCO$_3$ (25.2 g, 0.3 mol) in water (200 ml) was added. After heating to 45°, 4-methyl-1,2,4-triazolidin-5-oxo-3-thione (19.67 g, 0.15 mol) was added along with additional acetone (200 ml). The reaction was refluxed for 4 hours during which time the pH was maintained at ca. 7.2 by using 3N HCl as needed. The solution was cooled and adjusted to pH 3.5 which precipitated the product. The 7-amino-3-(4-methyl-5-oxo-$\Delta^2$-1,2,4-triazolin-3-ylthiomethyl)-3-cephem-4-carboxylic acid was collected, washed with water and acetone and dried.

This product was acylated with N-t-butoxycarbonylphenylglycine according to the procedure of Example 1 to give the t-butoxycarbonyl derivative of the title compound. This material was treated with cold trifluoroacetic acid for 15 minutes and concentrated in vacuo to a residue which was poured into ether. The solid trifluoroacetate salt was collected, dissolved in water and stirred with ion-exchange resin (Amberlite IR-45). After filtration, the aqueous solution was lyophilized to give the title compound.

EXAMPLE 4

7-Mandelamido-3-(4-methyl-5-oxo-$\Delta^2$-1,2,4-triazolin-3-ylthiomethyl)-3-cephem-4-carboxylic acid When 7-amino-3-(4-methyl-5-oxo-$\Delta^2$-1,2,4-triazolin-3-ylthiomethyl)-3-cephem-4-carboxylic acid (6.87 g, 0.02 mol) was reacted with O-dichloroacetylmandeloyl chloride (12.02 g, 0.043 mol) according to the procedure of Example 2, the title compound was obtained.

EXAMPLE 5

7-($\alpha$-Aminophenylacetamido)-3-(4-ethyl-5-oxo-$\Delta^2$-1,2,4-triazolin-3-ylthiomethyl)-3-cephem-4-carboxylic acid To a suspension of 7-ACA (21.78 g, 0.08 mol) in water (170 ml) and acetone (80 ml) was added a solution of NaHCO$_3$ (20.16 g, 0.24 mol) in water (160 ml) followed by 4-ethyl-3-thiono-5-oxo-$\Delta^2$-1,2,4-triazoline (17.42 g, 0.12 mol) and acetone (160 ml). The reaction was refluxed for 4 hours during which time the pH was maintained at ca. 7.2 by adding 3N HCl as needed. The solution was cooled and acidified to pH 3 which precipitated the product. The 7-aminocephalosporin nucleus was collected, washed with water and acetone, and dried.

The 7-aminocephalosporin nucleus (7.15 g, 0.02 mol) was acylated with N-t-butoxycarbonylphenylglycine (5.03 g, 0.02 mol) according to the procedure of Example 1 to give the N-protected derivative of the title compound. Using the method of Example 3 the protecting group was removed to give the title compound.

EXAMPLE 6

7-($\alpha$-Amino-p-hydroxyphenylacetamido)-3-(5-5-oxo-$\Delta^2$-1,2,4-triazolin-3-ylthiomethyl)-3-cephem-4-carboxylic acid the 7-aminocephalosporin nucleus from Example 1 (3.62 g, 0.011 mol) was acylated with N-t-butoxycarbonyl-p-hydroxyphenylglycine (2.67 g, 0.01 mol) according to the procedure of Example 1. The N-protected product was chromatographed on silica gel using 90:10:3 chloroform: methanol: formic acid as eluent. The pure solid was treated with cold trifluoroacetic acid for 15 minutes and then was concentrated and the residue was poured into ether. The solid trifluoroacetate salt was collected, dissolved in water and stirred with ion exchange resin (Amberlite IR-45). The filtered aqueous solution was lyophilized to give the title compound.

EXAMPLE 7

7-Mandelamido-3-(5-thiono-$\Delta^2$-1,3,4-thiadiazolin-2-ylthiomethyl)-3-cephem-4-carboxylic acid To a suspension of 7-ACA (20.6 g, 0.075 mol) and 1,3,4-thiadiazolidine-2,5-dithione in water (150 ml) and acetone (75 ml) was added a solution of NaHCO$_3$(24.2 g) in water (150 ml). Ether was added to control the foaming and was then distilled off when the addition was completed. The solution was refluxed for 2.75 hours, filtered, and conncentrated to remove the acetone. The cooled solution was acidified to pH 3 and the solid product was collected, washed with water and acetone, and dried.

The above product was acylated with 0-dichloroacetylmandeloyl chloride according to the procedure of Example 2 to give the desired product.

EXAMPLE 8

7-(α-Aminophenylacetamido)-3-(1-ethyl-5-oxo-$\Delta^2$-1,2,4-triazolin-3-ylthiomethyl)-3-cephem-4-carboxylic acid To a stirred solution of 7-ACA (14.9 g, 0.055 mol) in a mixture of water (110 ml) and acetone (55 ml) is added $NaHCO_3$ (12.27 g, 0.146 mol). The solution is warmed to 50° and a suspension of 1-ethyl-1,2,4-triazolidin-5-one-3-thione (11.9 g, 0.082 mol) in acetone (75 ml) was added slowly. The solution is adjusted to pH 7.5–8.0 and refluxed for 3.5 hours. The reaction is cooled and the solution adjusted to pH 3.5. The 7-aminocephalosporin nucleus is collected, washed with water and dried.

The 7-aminocephalosporin nucleus is acylated according to the procedure of Example 1 with N-t-butoxycarbonylphenylglycine to give the title compound.

EXAMPLE 9

7-Mandelamido-3-(1-ethyl-5-oxo-$\Delta^2$-1,2,4-triazolin-3-ylthiomethyl)-3-cephem-4-carboxylic acid Acylation of the 7-aminocephalosporin nucleus from Example 8 with 0-dichloroacetylmandeloyl chloride according to the procedure of Example 2 gives the title compound.

EXAMPLE 10

When 1-methyl-1,2,4-triazolidin-5-one-3-thione, 1,3,4-thiadiazolidin-5-one-2-thione, 1,2,4-triazolidin-3,5-dithione, 4-methyl-1,2,4-triazolidin-3,5-dithione, or 4-ethyl-1,2,4-triazolidin-3,5-dithione are substituted in the displacement reaction of Example 1 for 1,2,4-triazolidin-5-one-3-thione the following compounds are obtained:

7-Amino-3-(1-methyl-5-oxo-$\Delta^2$-1,2,4-triazolin-3-ylthiomethyl)-3-cephem-4-carboxylic acid 7-Amino-3-(5-oxo-$\Delta^2$-1,3,4-thiadiazolin-2-ylthiomethyl)-3-cephem-4-carboxylic acid 7-Amino-3-(5-thiono-$\Delta^2$-1,2,4-triazolin-3-ylthiomethyl)-3-cepehm-4-carboxylic acid 7-Amino-3-(4-methyl-5-thiono-$\Delta^2$-1,2,4-triazolin-3-ylthiomethyl)-3-cephem-4-carboxylic acid 7-Amino-3-(4-ethyl-5-thiono-$\Delta^2$-1,2,4-triazolin-3-ylthiomethyl)-3-cephem-4-carboxylic acid

EXAMPLE 11

When the 7-aminocephalosporins of Examples 7 and 10 are acylated with N-t-butoxycarbonylphenylglycine according to the procedure of Example 1, the following products are obtained:

7-(α-Aminophenylacetamido)-3-(5-thiono-$\Delta^2$-1,3,4-thiadiazolin-2-ylthiomethyl)-3-cephem-4-carboxylic acid 7-(α-Aminophenylacetamido)-3-(1-methyl-5-oxo-$\Delta^2$-1,2,4-triazolin-3-ylthiomethyl)-3-cephem-4-carboxylic acid 7-(α-Aminophenylacetamido)-3-(5-oxo-$\Delta^2$-1,3,4-thiadiazolin-2-ylthiomethyl)-3-cephem-4-carboxylic acid 7-(α-Aminophenylacetamido)-3-(5-thiono-$\Delta^2$-1,2,4-triazolin-3-ylthiomethyl)-3-cephem-4-carboxylic acid 7-(α-Aminophenylacetamido)-3-(4-methyl-5-thiono-$\Delta^2$-1,2,4-triazolin-3-ylthiomethyl)-3-cephem-4-carboxylic acid 7-(α-Aminophenylacetamido)-3-(4-ethyl-5-thiono$\Delta^2$-1,2,4-triazolin-3-ylthiomethyl)-3-cephem-4-carboxylic acid

EXAMPLE 12

Acylation of the 7-aminocephalosporins of Examples 5 and 10 with 0-dichloroacetylmandeloyl chloride according to the procedure of Example 2 gives the following products:

7-Mandelamido-3-(4-ethyl-5-oxo-$\Delta^2$-1,2,4-triazolin-3-ylthiomethyl)-3-cephem-4-carboxylic acid 7-Mandelamido-3-(1-methyl-5-oxo-$\Delta^2$-1,2,4-triazolin-3-ylthiomethyl)-3-cephem-4-carboxylic acid 7-Mandelamido-3-(5-oxo-$\Delta^2$-1,3,4-thiadiazolin-2-ylthiomethyl)-3-cephem-4-carboxylic acid 7-Mandelamido-3-(5-thiono-$\Delta^2$-1,2,4-triazolin-3-ylthiomethyl)-3-cephem-4-carboxylic acid 7-Mandelamido-3-(4-methyl-5-thiono-$\Delta^2$-1,2,4-triazolin-3-ylthiomethyl)-3-cephem-4-carboxylic acid 7-Mandelamido-3-(4-ethyl-5-thiono-$\Delta^2$-1,2,4-triazolin-3-ylthiomethyl)-3-cephem-4-carboxylic acid

EXAMPLE 13

The 7-aminocephalosporins of Examples 3, 5, 7, 8, and 10 are acylated with N-t-butoxycarbonyl-p-hydroxyphenylglycine according to the procedure of Example 6 to give the following compounds:

7-(α-Amino-p-hydroxyphenylacetamido)-3-(4-methyl-5-oxo-$\Delta^2$-1,2,4-triazolin-3-ylthiomethyl)-3-cephem-4-carboxylic acid 7-(α-Amino-p-hydroxyphenylacetamido)-3-(4-ethyl-5-oxo-$\Delta^2$-1,2,4-triazolin-3-ylthiomethyl)-3-cephem-4-carboxylic acid 7-(α-Amino-p-hydroxyphenylacetamido)-3-(5-thiono-$\Delta^2$-1,3,4-thiadiazolin-2-ylthiomethyl)-3-cephem-4-carboxylic acid 7-(α-Amino-p-hydroxyphenylacetamido)-3-(1-ethyl-5-oxo-$\Delta^2$-1,2,4-triazolin-3-ylthiomethyl-3-cephem-4-carboxylic acid 7-(α-Amino-p-hydroxyphenylacetamido)-3-(1-methyl-5-oxo-$\Delta^2$-1,2,4-triazolin-3-ylthiomethyl)-3-cephem-4-carboxylic acid 7-(α-Amino-p-hydroxyphenylacetamido)-3-(5-oxo-$\Delta^2$-1,2,4-triazolin-3-ylthiomethyl)-3-cephem-4-carboxylic acid 7-(α-Amino-p-hydroxyphenylacetamido)-3-(5-thiono-$\Delta^2$-1,2,4-triazolin-3-ylthiomethyl)-3-cephem-4-carboxylic acid 7-(α-Amino-p-hydroxyphenylacetamido)-3-(4-methyl-5-thiono-$\Delta^2$-1,2,4-triazolin-3-ylthiomethyl)-3-cephem-4-carboxylic acid 7-(α-Amino-p-hydroxyphenylacetamido)-3-(4-ethyl-5-thiono-$\Delta^2$-1,2,4-triazolin-3-ylthiomethyl)-3-cephem-4-carboxylic acid

EXAMPLE 14

A solution of p-hydroxymandelic acid (3.0 g, 0.018 mol) and N-trimethylsilylacetamide (5.31 g, 0.042 mol) in dry THF (60 ml) and triethylamine (3ml) is refluxed in a nitrogen atmosphere for 2 hours, cooled to −10° and then treated with isobutyl chloroformate and 1,2,4-triazolidin-5-one-3-thione as in Example 1. The reaction solution is concentrated to a turbid aqueous mixture which is treated with 3% $NAHCO_3$ until a clear solution is obtained. Water is added and the aqueous solution is washed with ether. The aqueous layer is cooled, covered with ethyl acetate and acidified to pH 1.5 with 6 N HCl. Phases are separated and the aqueous layer is reextracted with fresh ethyl acetate. The combined extracts are dried and concentrated to give 7-(p-hydroxymandelamido)-3-(5-oxo-$\Delta^2$-1,2,4-triazolin-3-ylthiomethyl)-3-cephem-4-carboxylic acid.

When any of the 7-aminocephalosporins in Examples 3, 5, 7, 8, and 10 are acylated with p-hydroxymandelic acid according to the above procedure the analogous products are obtained.

EXAMPLE 15

When the N-t-butoxycarbonyl derivative of p-methoxyphenylglycine, m-methoxyphenylglycine, o-methoxyphenylglycine, or p-methylthiophenylglycine is substituted for N-t-butoxycarbonylphenylglycine in the procedure of Example 1 the corresponding 7-($\alpha$-amino-substituted phenylacetamido)-3-(5-oxo-$\Delta^2$-1,2,4-triazolin-3-ylthiomethyl)-3-cephem-4-carboxylic acid is obtained.

EXAMPLE 16

Using the procedure of Example 2 with the dichloroacetyl derivative of p-methoxymandelic acid, m-methoxymandelic acid, o-methoxymandelic acid, or p-methylthiomandelic acid gives the appropriate 7-substituted mandelamido-3-(5-oxo-$\Delta^2$-1,2,4-triazolin-3-ylthiomethyl)-3-cephem-4-carboxylic acid.

EXAMPLE 17

An equimolar amount of N-t-butoxycarbonyl-p-hydroxymethylphenylglycine, N-hydroxysuccinimide, and dicyclohexylcarbodiimide in dry THF is stirred at 0° for 7 hours. The reaction is filtered and the filtrate is evaporated to give the activated ester.

To a cooled solution of 7-amino-3-(5-oxo-$\Delta^2$-1,2,4-triazolin-3-ylthiomethyl)-3-cephem-4-carboxylic acid (7.57 g, 0.023 mol) in pyridine (120 ml) containing triethylamine (5.5 ml) is added the activated ester (8.70 g, 0.023 mol). The reaction is stirred at room temperature for 5 hours and poured into water. The aqueous solution was adjusted to pH 2 and the t-butoxycarbonyl derivative is collected. Treatment with trifluoroacetic acid as in Example 1 gives 7-($\alpha$-amino-p-hydroxymethylphenylacetamido)-3-(5-oxo-$\Delta^2$-1,2,4-triazolin-3-ylthiomethyl)-3-cephem-4-carboxylic acid.

Acylation of the other 7-aminocephalosporins of Examples 3, 5, 7, 8 and 10 with p-hydroxymethylphenylglycine by the above procedure gives the corresponding products.

EXAMPLE 18

When esters of 7-ACA, such as 2,2,2-trichloroethyl, benzhydryl, t-butyl, p-nitrophenyl, p-methoxyphenyl, p-methoxybenzyl, or benzyloxymethyl, are reacted with the heterocyclicthione compounds according to the procedure of Example 1, the corresponding 7-amino-3-heterocyclicthiomethylcephem ester is obtained. The esters can be acylated in the same manner as is described above for the acids, followed by cleavage of the ester moiety by standard methods, to give the product compounds of this invention.

What is claimed is:

1. A compound of the formula

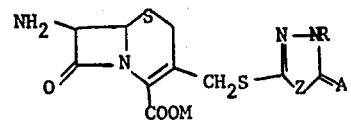

wherein Z is S;

A is O or S;

R is hydrogen or $C_1$-$C_4$ alkyl; and

M is hydrogen, 2,2,2-trichloroethyl, benzhydryl, t-butyl, p-nitrophenyl, p-methoxyphenyl, p-methoxybenzyl, or benzyloxymethyl.

2. A compound as claimed in claim 1 where Z and A are S.

3. A compound as claimed in claim 2 being the compound 7-amino-3-(5-thiono-$\Delta^2$-1,3,4-thiadiazolin-2-ylthiomethyl)-3-cephem-4-carboxylic acid.

* * * * *

UNITED STATES PATENT AND TRADEMARK OFFICE
CERTIFICATE OF CORRECTION

PATENT NO. : 3,943,129
DATED : March 9, 1976
INVENTOR(S) : David A. Berges

It is certified that error appears in the above-identified patent and that said Letters Patent are hereby corrected as shown below:

Column 4, line 13: "dissolved in 7-ACA" should read -- dissolved 7-ACA --

Column 6, line 37: "3-(5-5-oxo-" should read -- 3-(5-oxo- --

Column 6, line 41: "the" should read -- The --

Signed and Sealed this

Twentieth Day of July 1976

[SEAL]

Attest:

RUTH C. MASON
*Attesting Officer*

C. MARSHALL DANN
*Commissioner of Patents and Trademarks*